United States Patent
Tang et al.

(10) Patent No.: US 9,957,237 B2
(45) Date of Patent: May 1, 2018

(54) CRYSTAL FORM OF NEPTINIB DI-P-METHYLBENZENESULFONATE, PREPARATION METHOD THEREOF, AND PHARMACEUTICAL COMPOSITION CONTAINING SAME

(71) Applicant: SHENZHEN NEPTUNUS PHARMACEUTICAL RESEARCH INSTITUTE CO., LTD., Shenzhen (CN)

(72) Inventors: Tian Tang, Shenzhen (CN); Feng Jin, Shenzhen (CN); Yanqing Wang, Shenzhen (CN); Jing Wu, Shenzhen (CN); Xiarou Liu, Shenzhen (CN); Jing'an Yang, Shenzhen (CN); Hanlin Feng, Shenzhen (CN); Lin Yu, Shenzhen (CN)

(73) Assignee: SHENZHEN NEPTUNUS PHARMACEUTICAL RESEARCH INSTITUTE CO., LTD., Shenzhen (CN)

( * ) Notice: Subject to any disclaimer, the term of this patent is extended or adjusted under 35 U.S.C. 154(b) by 0 days. days.

(21) Appl. No.: 15/539,070

(22) PCT Filed: Dec. 22, 2015

(86) PCT No.: PCT/CN2015/098239
§ 371 (c)(1),
(2) Date: Jun. 22, 2017

(87) PCT Pub. No.: WO2016/101867
PCT Pub. Date: Jun. 30, 2016

(65) Prior Publication Data
US 2017/0342037 A1 Nov. 30, 2017

(30) Foreign Application Priority Data

Dec. 25, 2014 (CN) .......................... 2014 1 0822395

(51) Int. Cl.
A61K 31/517 (2006.01)
C07D 239/94 (2006.01)
C07C 309/30 (2006.01)

(52) U.S. Cl.
CPC .......... *C07D 239/94* (2013.01); *C07C 309/30* (2013.01); *C07B 2200/13* (2013.01)

(58) Field of Classification Search
CPC ........................... A61K 31/517; C07D 239/94
USPC ....................................... 514/266.4; 544/293
See application file for complete search history.

(56) References Cited

FOREIGN PATENT DOCUMENTS

WO  WO 2007/085638  *  8/2007

* cited by examiner

*Primary Examiner* — Brenda L Coleman
(74) *Attorney, Agent, or Firm* — Greer, Burns & Crain, Ltd.

(57) ABSTRACT

Provided is a composition of N-[4-[(3-chloro-4-fluorophenyl)amino]-7-[3-(ethoxy)-6-quinazolinyl]-4-(dimethylamino)-2-butenamide p-toluene sulfonate 1.5 hydrate α-polymorph. The α-polymorph has a stable form, a defined melting point, a good chemical stability, and a good endurance to high temperature and light irradiation, and is suitable for pharmaceutical use.

8 Claims, 5 Drawing Sheets

CRYSTAL FORM OF NEPTINIB DI-P-METHYLBENZENESULFONATE, PREPARATION METHOD THEREOF, AND PHARMACEUTICAL COMPOSITION CONTAINING SAME

BACKGROUND

The present invention belongs to the field of medicine technology, and particularly relates to a new crystal form of crystalline hydrate of Neptinib di-p-methylbenzenesulfonate.

The crystalline hydrate of compound (E)-N-(4-((3-chloro-4-fluorophenyl)amino)-7-ethoxyquinazolin-6-yl)-4-(dimethylamino)but-2-enamide (Neptinib) di-p-methylbenzene sulfonate represented by Formula (1) is useful in the treatment of hyperproliferative diseases, such as cancer, in mammals.

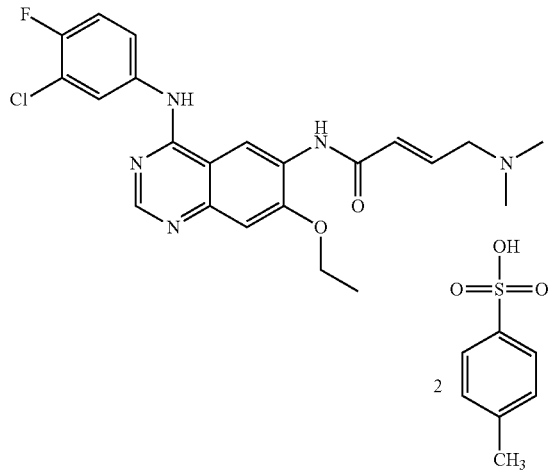

Formula (1)

The compound is an inhibitor of tyrosine kinase such as epidermal growth factor receptor and can be used to treat or prevent a disease related to tyrosine kinase such as epidermal growth factor receptor, such as cancer, especially non-small cell lung cancer, colorectal cancer, refractory non-small cell lung cancer, ovarian cancer, pancreatic cancer, breast cancer, neuroglioma tumor, brain tumor, or neck cancer.

SUMMARY

An object of the invention is to provide a new crystal form of crystalline hydrate of (E)-N-(4-((3-chloro-4-fluorophenyl)amino-7-ethoxyquinazolin-6-yl)-4-dimethylamino)but-2-enamide (Neptinib) di-p-methylbenzenesulfonate, which is characterized by melting point, X-ray powder diffraction (XRD), differential scanning calorimetiy (DSC) and thermogravimetric analysis (TG), infrared spectrum (IR) and elemental analysis, and the crystal form has the properties required by solid pharmaceutical preparations.

A second object of the present invention is to provide a method for preparing the new crystal form of crystalline hydrate of (E)-N-(4-((3-chloro-4-fluorophenyl)amino)-7-ethoxyquinazolin-6-yl)-4-(dimethylamino)but-2-enamide (Neptinib) di-p-methylbenzene sulfonate.

Another object of the present invention is to provide a pharmaceutical composition containing the new crystal form of crystalline hydrate of (E)-N-(4-((3-chloro-4-fluorophenyl)amino)-7-ethoxyquinazolin-6-yl)-4-(dimethylamino) but-2-enamide (Neptinib) di-p-methylbenzenesulfonate.

During the preparation of the crystalline hydrate of (E)-N-(4-((3-chloro-4-fluorophenyl)amino)-7-ethoxyquinazolin-6-yl)-4-(dimethylamino)but-2-enamide (Neptinib) di-p-methylbenzenesulfonate, the inventors obtained a new crystal form of 1.5 hydrate, designated as Form α, by recrystallization of crude product of the compound. By measuring the melting point and subjecting to X-ray powder diffraction, DSC, TG, IR and elemental analysis, the crystal obtained has been confirmed to be a new form, and designated as crystal form α of (E)-N-(4-((3-chloro-4-fluorophenyl)amino)-7-ethoxy quinazolin-yl)-4-(dimethylamino)but-2-enamide(Neptinib)di-p-methylbenenesulfonate 1.5 hydrate.

According to one aspect of the present invention, the crystal form α of (E)-N-(4-((3-chloro-4-fluorophenyl)amino)-7-ethoxyquinazolin-6-yl)-4-(dimethylamino)but-2-enamide (Neptinib) di-p-methylbenzenesulfonate 1.5 hydrate, when subjected to X-ray powder diffraction with a Cu radiation source, said crystal form α comprises characteristic diffraction peaks at 2θ of 5.0±0.2, 17.6±0.2, 18.7±0.2 (°), and each of the peaks has a relative intensity of greater than or equal to 20%. Further, said crystal form may also comprise characteristic diffraction peaks at 2θ of 12.1±0.2, 14.5±0.2, 15.6±0.2, 20.1±0.2, 22.0±0.2, 25.4±0.2, 26.0±0.2 and 26.3±0.2 (°) in the X-ray powder diffraction pattern, and each of the peaks has a relative intensity of greater than or equal to 7% (see FIG. 1).

Wherein, "±0.2" is an allowable measurement error range.

The crystal form α of the present invention can be characterized by an X-ray powder diffraction pattern. It is characterized that the X-ray powder diffraction pattern has characteristic diffraction peaks at 2θ° described above, and the relative intensity is close to the following values:

| | Item | | |
|---|---|---|---|
| No. | 2θ° | d-spacing | I/I$_0$(Relative intensity) |
| 1 | 5.0280 | 17.57597 | 100% |
| 2 | 12.1417 | 7.28963 | 13.90% |
| 3 | 14.5223 | 6.09959 | 7.69% |
| 4 | 15.6252 | 5.67143 | 8.19% |
| 5 | 17.6798 | 5.01672 | 41.02% |
| 6 | 18.7496 | 4.73282 | 25.08% |
| 7 | 20.1191 | 4.41364 | 7.48% |
| 8 | 22.0733 | 4.02711 | 8.89% |
| 9 | 25.4152 | 3.50465 | 7.29% |
| 10 | 26.0953 | 3.41483 | 7.39% |
| 11 | 26.3735 | 3.37944 | 11.13% |

The term "close" herein refers to the uncertainty of measurement values of the relative intensity. The persons skilled in the art understand that the uncertainty of the relative intensity is very dependent on the measurement conditions. The relative intensity values may be altered, for example, in the range of ±25% or preferably altered in the range of ±10%.

The crystal form α described above has an X-ray powder diffraction pattern shown in FIG. 1.

The crystal form α of (E)-N-(4-((3-chloro-4-fluorophenyl)amino)-7-ethoxy quinazolin-6-yl)-4-(dimethylamino)but-2-enamide (Neptinib) di-p-methylbenzenesulfonate 1.5 hydrate of the present invention is characterized by differential scanning calorimetry technique (DSC) (see FIG. 2), wherein the differential scanning calorimetry pattern has an endothermic maximum at 133° C. The endothermic process shows an endothermic peak in the DSC pattern.

The crystal form α of (E)-N-(4-((3-chloro-4-fluorophenyl)amino)-7-ethoxy quinazolin-6-yl)-4-(dimethylamino)but-2-enamide (Neptinib) di-p-methylbenzenesulfonate 1.5 hydrate of the present invention is characterized by thermogravimetric analysis technique (see FIG. 3), wherein the thermogravimetric pattern (TG) shows a weight loss of 2.5% at 169° C., indicating the loss of crystalline water under this temperature.

The crystal form α of the 1.5 hydrate of the present invention has an infrared spectrum shown in FIG. 4, comprising relatively strong absorption peaks at 3419, 3284, 3052, 2930, 2732, 2589, 1695, 1640, 1575, 1543, 1524, 1498, 1452, 1400, 1368, 1328, 1266, 1238, 1218, 1185, 1160, 1121, 1033, 1008, 814, 684, 568, 500 $cm^{-1}$.

The element analysis data of the crystal form α of the present invention are in agreement with the theoretical values (with difference within ±0.3%), which further confirms that the compound contains 1.5 crystal water (see table below).

| Sample No. | Element content (%) | | | |
|---|---|---|---|---|
| | C | H | N | S |
| 1 | 53.15 | 5.04 | 8.57 | 7.68 |
| Theoretical value | 53.03 | 5.19 | 8.59 | 7.87 |

According to another aspect of the invention, the method for preparing the crystal form α of (E)-N-(4-(3-chloro-4-fluorophenyl)amino)-7-ethoxyquinazolin-6-yl)-4-(dimethylamino)but-2-enamide (Neptinib) di-p-methylbenzenesulfonate 1.5 hydrate comprises: adding crude product of (E)-N-4-((3-chloro-4-fluorophenyl)amino)-7-ethoxy quinazolin-6-yl)-4-(dimethylamino)but-2-enamide (Neptinib) di-p-methylbenzenesulfonate into a mixed solvent of $C_1$-$C_4$ alkyl alcohol and water or into a mixed solvent of $C_3$-$C_4$ alkyl ketone and water, heating under reflux to achieve dissolution; cooling the clear solution to precipitate, filtrating, collecting the precipitate, and drying the collected precipitate under reduced pressure to obtain the crystal form α. Said alcohol is selected from the group consisting of methanol, ethanol, propanol, isopropanol and butanol, and is preferably ethanol; and the volume ratio (V/V) of alcohol to water is 11:1~20:1; said ketone is selected from the group consisting of acetone, methyl ethyl ketone and butanone and the like, and is preferably acetone, and the volume ratio (V/V) of ketone to water is 11:1~20:1. The weight volume ratio (W/V) of the crude product to the solvent is 1 (g):5~30 (ml), and is preferably 1:12 (g/ml). The solution is preferably heated to 50~80° C., and more preferably, the mixture of alcohol and water is heated to 70° C., the mixture of ketone and water is heated to 60° C. According to this embodiment, the precipitation is carried out for 2~8 hours, and preferably 4 hours. The precipitation temperature is 0~40° C., and preferably 5~15° C. After the completion of precipitation, the obtained precipitate is dried at a temperature of 30~60° C., and preferably 45° C.

According to another aspect of the invention, a pharmaceutical composition comprising the crystal form α of (E)-N-(4-((3-chloro-4-fluorophenyl)amino)-7-ethoxy quinazolin-6-yl)-4-(dimethylamino)but-2-enamide (Neptinib) di-p-methylbenzenesulfonate 1.5 hydrate is provided. The composition comprises the new crystal form of the compound and optionally pharmaceutically acceptable carriers and/or excipients.

The pharmaceutical composition may be further formulated according to a conventional preparation method into an administration form, including oral or parenteral administration form. The administration form should contain a therapeutically effective amount of the crystal form α of (E)-N-(4-((3-chloro-fluorophenyl)amino)-7-ethoxyquinazolin-6-yl)-4-(dimethylamino)but-2-enamide (Neptinib) di-p-methylbenzenesulfonate. The so-called "therapeutically effective amount" means that the compound of the present invention at this dose can improve or relieve the symptoms of a disease or can inhibit or block the development of a disease.

According to the experiences and considering the standard methods and references in the art, the persons skilled in this art can easily select various carriers and/or excipients and determine the dose.

The application scope of the crystal form α of (E)-N-(4-((3-chlor-4-fluorophenyl)amino)-7-ethoxyquinazolin-yl)-4-(dimethylamino)but-2-enamide(Neptinib)di-p-methylbenzene sulfonate is identical to that of Neptinib di-p-methylbenzenesulfonate, which is used for the treatment of hyperproliferative diseases. Preferably, the hyperproliferative disease is cancer, including but not limited to non-small cell lung cancer, colorectal cancer, refractory non-small cell lung cancer, pancreatic cancer, ovarian cancer, breast cancer, neuroglioma tumor, brain cancer, or neck cancer.

The crystal form α of (E)-N-(4-((3-chloro-4-fluorophenyl)amino)-7-ethoxy quinazolin-6-yl)-4-(dimethylamino)but-2-enamide(Neptinib)di-p-methylbenzenesulfonate obtained by the present invention has a stable form, a defined melting point, good chemical stability, and good endurance to high temperature and light irradiation. The new crystal form of (E)-N-4-((3-chloro-1-fluorophenyl)amino)-7-ethoxyquinazolin-6-yl)-4-(dimethylamino)but-2-enamide (Neptinib) di-p-methylbenzenesulfonate has the desirable properties for preparing a solid preparation, and is favorable for storage, easy to be produced, and its quality is easier to be controlled.

DETAILED DESCRIPTION

All materials and reagents were commercially available.
Preparation of crude product:
(E)-N-(4-((3-chloro-4-fluorophenyl)amino)-7-ethoxyquinazolin-6-yl)-4-(dimethylamino)but-2-enamide(Neptinib) was prepared using N-3-chloro-4-fluorophenyl)amino]-7-fluor-6-nitro-4-quinazolinamine as a starting material with reference to method of the patent publication WO2007085638, and the salt-forming process was performed with reference to the method of the patent publication WO2012121764.

Preparation of crystal form α of (E)-N-(4-((3-chloro-4-fluorophenyl)amino)-7-ethoxy quinazolin-6-yl-4-(dimethylamino)but-2-enamide (Neptinib) di-p-methylbenzenesulfonate Example 1

200 g of crude Neptinib di-p-methylbenzenesulfonate was added into a reaction flask, and 2400 ml of mixture of acetone and water (V/V=12:1) was added, refluxed at 60° C. under stirring. After the solid was dissolved, the solution was stirred for 10 min, cooled to 5~15° C. to precipitate, stirred for another 4 hours for crystallization, and filtrated. The filter cake was leached with acetone, and then subjected to air blast drying at 45° C. with the assistance of phosphorus pentoxide. 163 g of whitish solid was obtained, with a yield of 81.5%. The water content was determined to be 3.3% by Karl Fischer titrator. The obtained compound was crystal form α of (E)-N-(4-((3-chloro-4-fluorophenyl)amino)-7-ethoxyquinazolin-yl)-4-(dimethylamino)but-2-enamide (Neptinib) di-p-methylbenzene sulfonate 1.5 hydrate.

Figure 1:
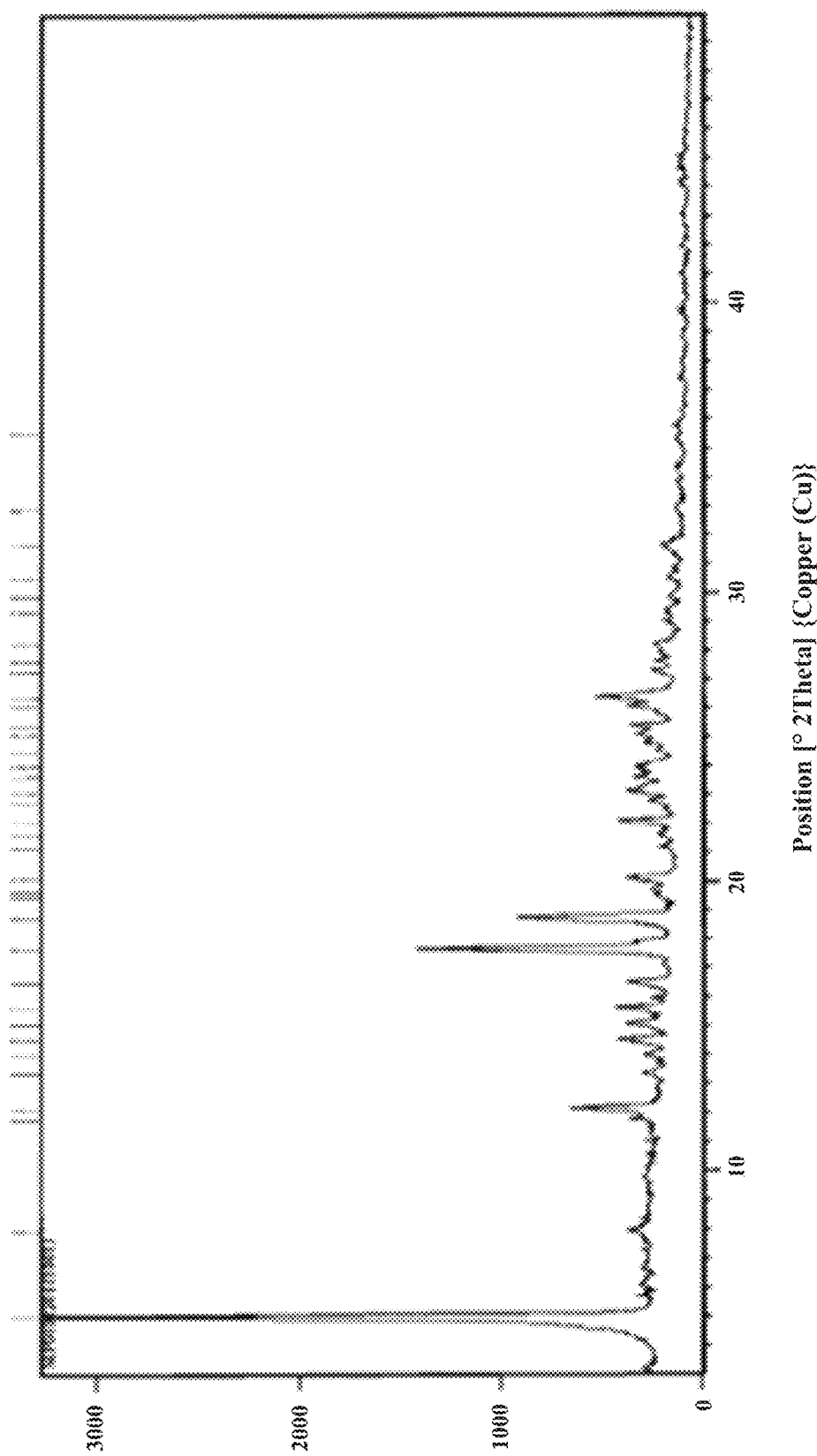
FIG. 1 is an X-ray diffraction pattern of the α-polymorph obtained in Example 1 of the present invention.
Figure 2:
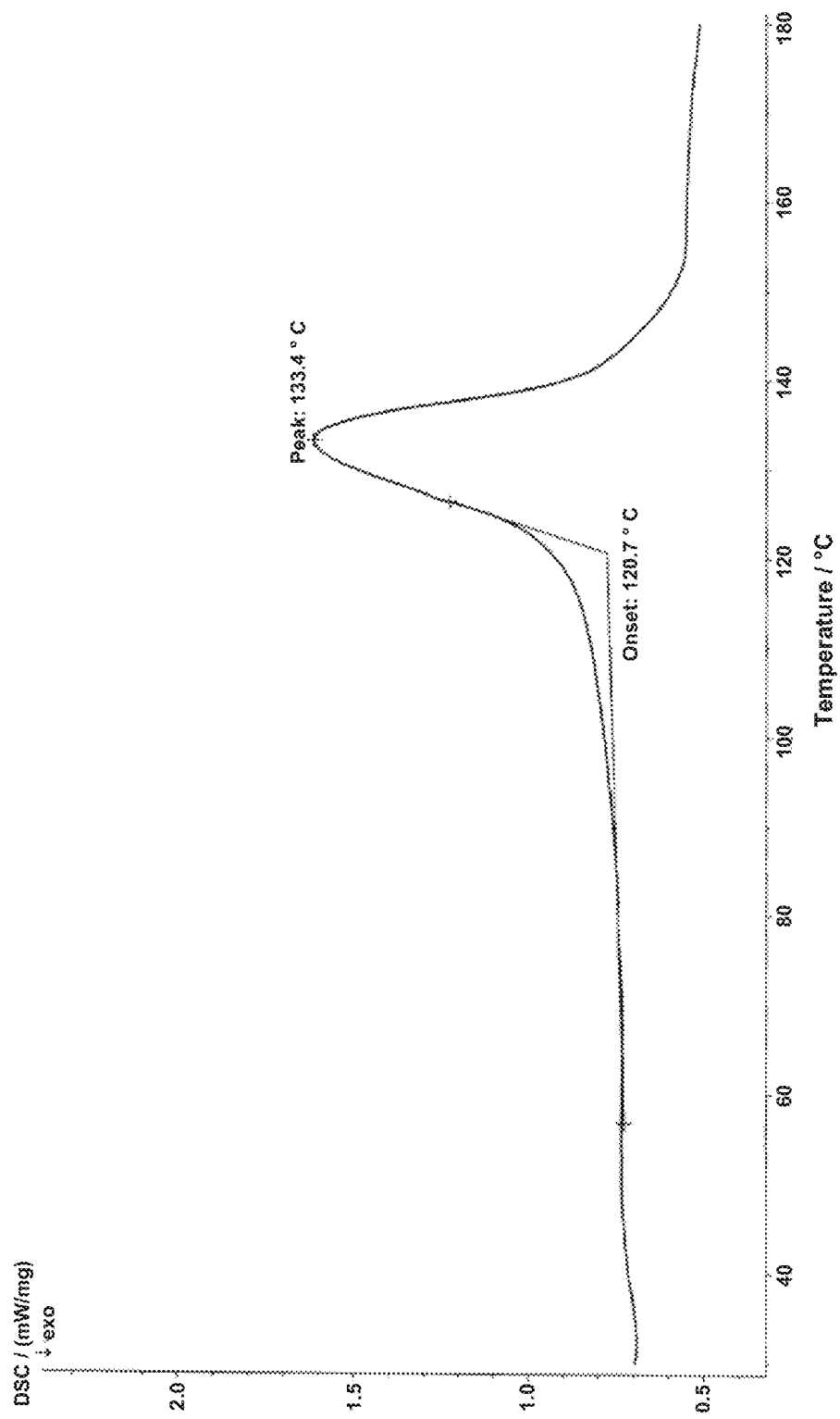
FIG. 2 is a DSC pattern of the α-polymorph obtained in Example 1 of the present invention.
Figure 3:
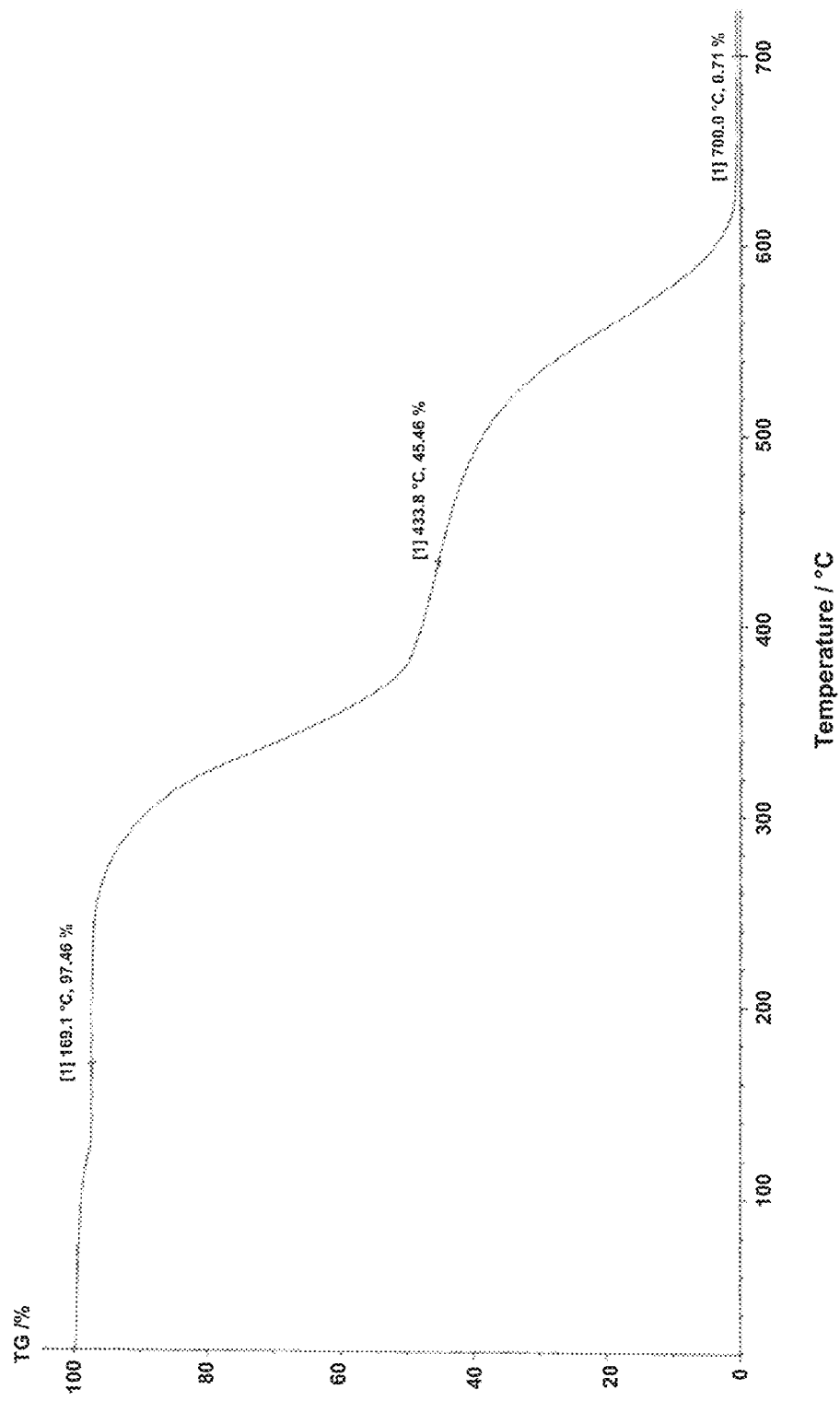
FIG. 3 is a TG pattern of the α-polymorph obtained in Example 1 of the present invention.
Figure 4:
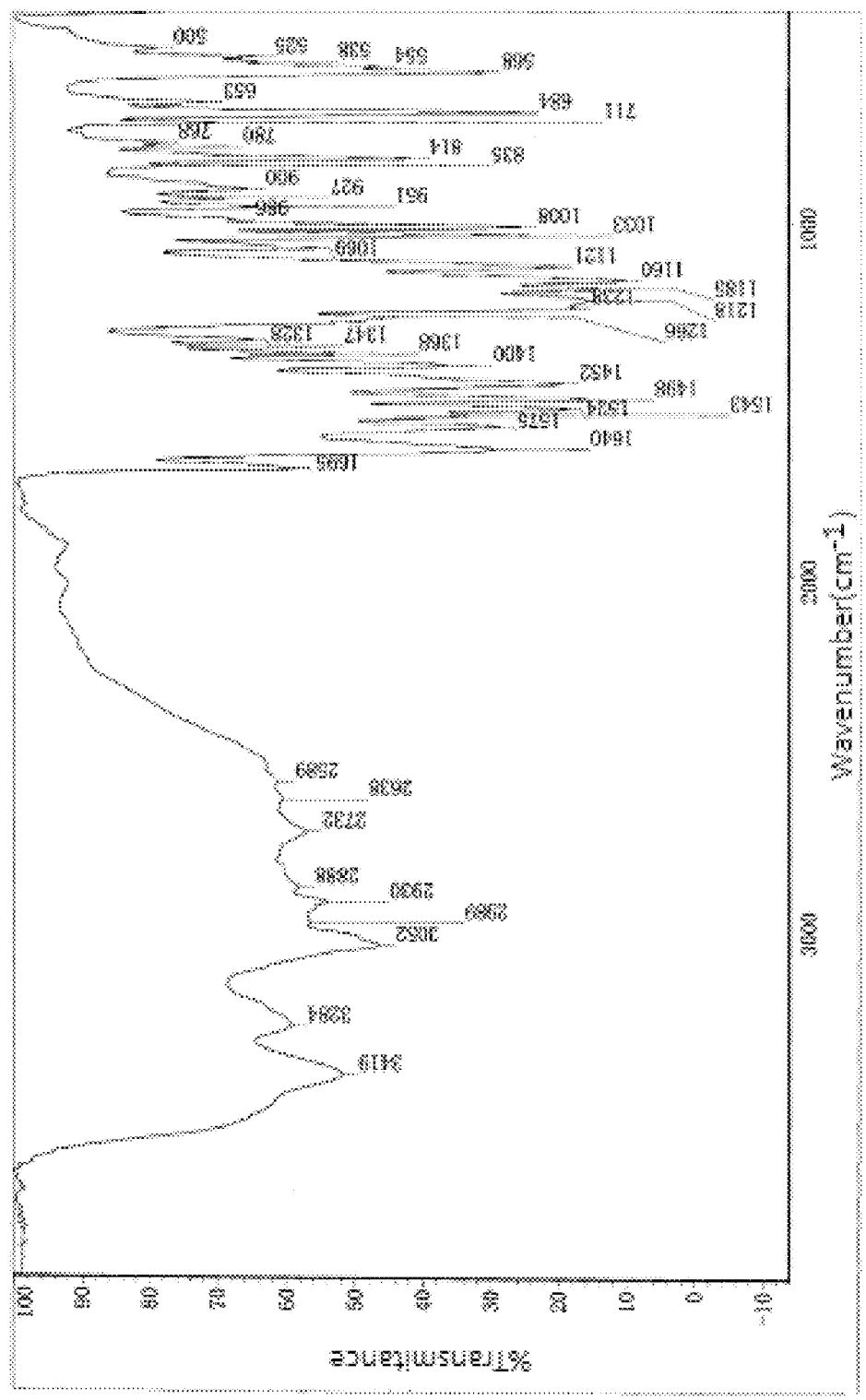
FIG. 4 is an IR spectrum of the α-polymorph obtained in Example 1 of the present invention.
Figure 5:
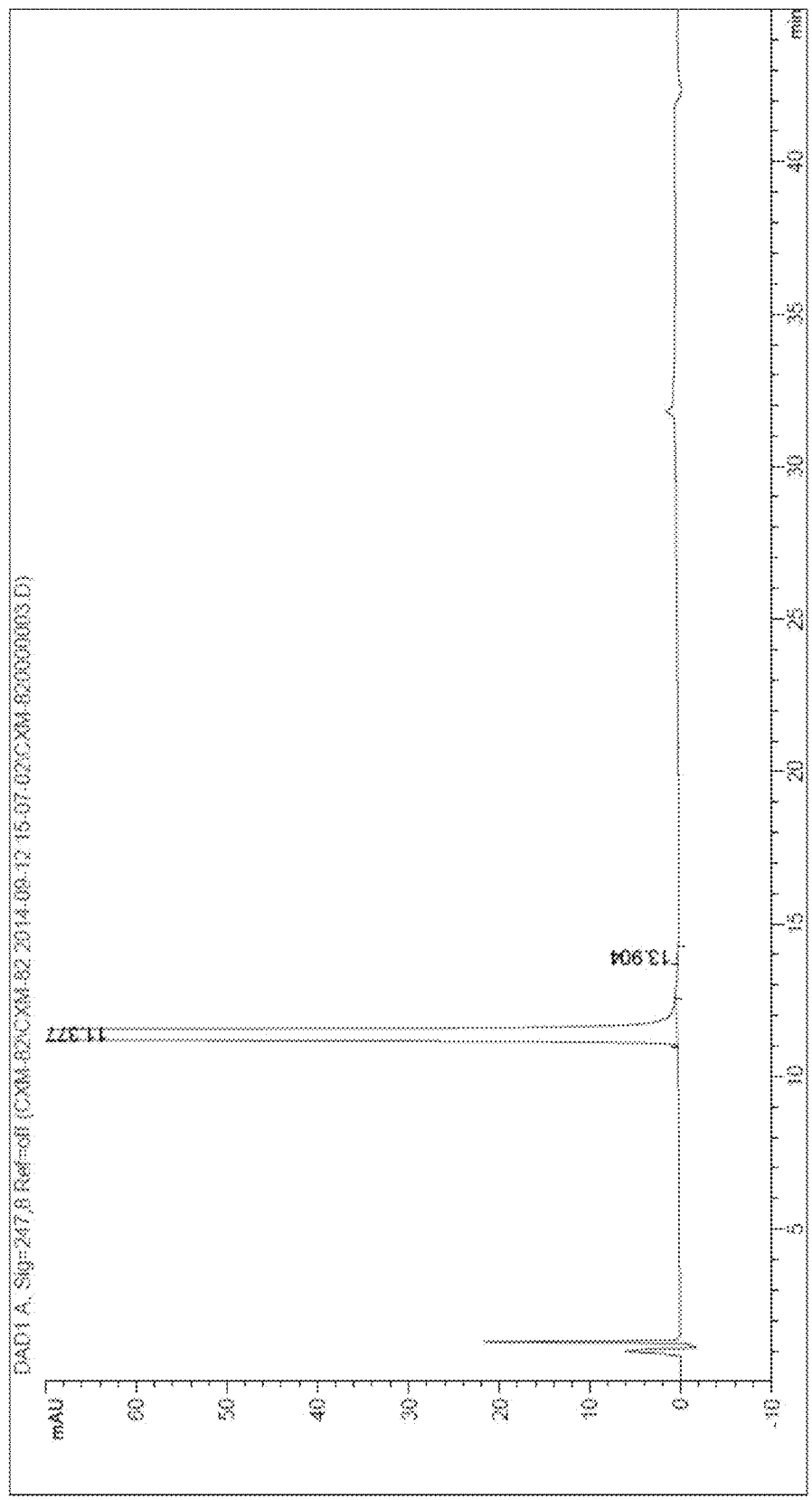
FIG. 5 is an HPLC pattern of the α-polymorph obtained in Example 1 of the present invention.

The characteristics of the compound were identified as shown in FIGS. 1 to 5.

Test conditions for the samples of the example:

(1) XRD:
Detection instrument: Empyrean X-ray diffractometer
Detection conditions: Cu target Kα ray, Voltage 40 kV, Current 40 mA, Divergence slit 1/32°, Anti-scatter slit 1/16°, Anti scatter slit 7.5 mm, 2θ range: 3°-50°, Step size 0.02°, step motion time: 40 s/step.
Detection method: X-ray powder diffraction method, Appendix IX F, Pharmacopoeia of the People's Republic of China (2010 Edition, Part II)
Detection result: see FIG. 1.

(2) DSC:
Detection instrument: DSC 204F1 differential scanning calorimeter, NETZSCH Company, Germany
Detection conditions: Atmosphere: $N_2$ (purity: ≥99.99), 20 ml/min; Scanning procedure: heating rate of 10° C./min from room temperature to 180° C., recording the temperature curve; Sample quality: Sample 1: 2.27 mg (Aluminum sample tray)
Detection method: General rules for thermal analysis JY/T 014-1996
Detection result: see FIG. 2.

(3) TG:
Detection instrument: TG209 thermal gravimetric analyzer, NETZSCH company, Germany
Detection conditions: Atmosphere: air, 20 ml/min; Scanning procedures: room temperature 700° C., heating rate: 10° C./min.
Detection method: General rules for thermal analysis JY/T 014-1996
Detection result: see FIG. 3.

(4) Infrared spectrum:
Detection instrument: FT-IR NICOLET6700 (Germany)
Detection conditions: potassium bromide disc
Detection method: General rules for infrared analysis GB/T 6040-2002
Detection result: see FIG. 4.

(5) HPLC
Detection instrument: Agilent 1260 series (U.S.)
Detection conditions: Chromatographic column: Waters C18; Mobile phase A: acetonitrile-mobile phase B (70:30); Mobile phase B: 0.05 mol/l ammonium dihydrogen phosphate solution (pH=7.3); Column temperature: 30° C.; Detection wavelength: 247 nm.
Detection method: High performance liquid chromatography method, Pharmacopoeia of the People's Republic of China, Part II Appendix VD
Detection result: see FIG. 5.

Example 2

200 g of crude Neptinib di-p-methylbenzenesulfonate was added into a reaction flask, and 1600 ml of mixed solvent of acetone and water (V/V=10:1) was added, refluxed at 60° C. under stirring. After the solid was dissolved, the solution was stirred for 10 min, cooled to 5~15° C. to precipitate, stirred for another 4 hours for crystallization, and filtrated. The filter cake was leached with acetone, and then subjected to air blast drying at 45° C. with the assistance of phosphorus pentoxide. 154 g of whitish solid was obtained with a yield of 77%. The water content was determined to be 4.4% by Karl Fischer titrator. The obtained compound was crystal form β of (E)-N-(4-((3-chloro-4-fluorophenyl)amino)-7-ethoxyquinazolin-6-yl)-4-(dimethylamino)but-2-enamide (Neptinib) di-p-methylbenzene sulfonate 2 hydrate.

Other Examples 20 g of Neptinib di-p-methylbenzenesulfonate was respectively added into a reaction flask, and the experiments were carried out with reference to the experiment operations of Examples 1~2:

| No. | Organic solvent | Solvent/water (V/V) | Crude product/mixed solvent (g/ml) | Heat temp. (° C.) | Precipitation temp. (° C.) | Precipitation time (h) | Dry temp. (° C.) | Yield (%) | Water (%) |
|---|---|---|---|---|---|---|---|---|---|
| 3 | Ethanol | 1:1 | 1 g:5 ml | 50 | 0~5 | 2 | 45 | 52 | 4.6 |
| 4 | Ethanol | 5:1 | 1 g:18 ml | 65 | 5~15 | 3 | 30 | 58.3 | 4.5 |
| 5 | Ethanol | 10:1 | 1 g:30 ml | 70 | 15~25 | 4 | 60 | 60.7 | 4.4 |
| 6 | Ethanol | 12:1 | 1 g:5 ml | 70 | 15~25 | 4 | 60 | 65 | 3.4 |
| 7 | Ethanol | 15:1 | 1 g:18 ml | 75 | 25~40 | 6 | 30 | 47.8 | 3.3 |
| 8 | Ethanol | 20:1 | 1 g:30 ml | 80 | 15~25 | 8 | 45 | 56.1 | 3.2 |
| 9 | Methanol | 5:1 | 1 g:15 ml | 65 | 0~5 | 2 | 60 | 52.7 | 4.5 |
| 10 | Methanol | 10:1 | 1 g:18 ml | 70 | 15~25 | 4 | 45 | 52 | 4.4 |
| 11 | Methanol | 15:1 | 1 g:25 ml | 75 | 5~15 | 6 | 50 | 60.3 | 3.3 |
| 12 | Methanol | 20:1 | 1 g:30 ml | 80 | 25~40 | 8 | 50 | 51.6 | 3.2 |
| 13 | Isopropyl | 6:1 | 1 g:15 ml | 70 | 0~5 | 4 | 45 | 45.3 | 4.4 |

-continued

| No. | Organic solvent | Solvent/ water (V/V) | Crude product/ mixed solvent (g/ml) | Heat temp. (° C.) | Precipitation temp. (° C.) | Precipitation time (h) | Dry temp. (° C.) | Yield (%) | Water (%) |
|---|---|---|---|---|---|---|---|---|---|
| 14 | Butanol alcohol | 12:1 | 1 g:20 ml | 80 | 15~25 | 5 | 55 | 42.8 | 3.3 |
| 15 | Propanol | 18:1 | 1 g:12 ml | 75 | 25~40 | 6 | 60 | 44.7 | 3.2 |
| 16 | Acetone | 1:1 | 1 g:5 ml | 80 | 0~5 | 4 | 60 | 70 | 4.5 |
| 17 | Acetone | 5:1 | 1 g:5 ml | 70 | 25~40 | 5 | 45 | 71.3 | 4.3 |
| 18 | Acetone | 8:1 | 1 g:8 ml | 75 | 15~25 | 6 | 50 | 74.5 | 4.6 |
| 19 | Acetone | 10:1 | 1 g:11 ml | 60 | 5~15 | 4 | 45 | 89 | 4.4 |
| 20 | Acetone | 12:1 | 1 g:12 ml | 60 | 15~25 | 8 | 45 | 85.6 | 3.3 |
| 21 | Acetone | 15:1 | 1 g:30 ml | 50 | 0~5 | 4 | 40 | 74 | 3.2 |
| 22 | Butanone | 1:1 | 1 g:5 ml | 50 | 0~5 | 2 | 30 | 43.8 | 4.4 |
| 23 | Methyl ethyl ketone | 20:1 | 1 g:30 ml | 80 | 25~40 | 8 | 60 | 49.6 | 3.1 |

Stability studies on crystal forms of (E)-N-(4-((3-chloro-4-fluorophenyl)amino)-7-ethoxyquinazolin-6-yl)-4-dimethylamino)but-2-enamide (Neptinib) di-p-methylbenzene sulfonate Example 3

The stability studies of crystal forms α and β (accelerated test for 10 days) were performed respectively under the conditions of 40° C., 60° C., relative humidity 75%, 92.5%, and light irradiation, to compare the data of water content, purity, maximum single impurity and total impurities of the new crystal form with that on the day 0, and the results showed that the obtained crystal form is stable. The free base (E)-N-(4-((3-chloro-4-fluorophenyl)amino)-7-ethoxyquinazolin-6-yl)-4-(dimethylamino)but-2-enamide was obviously degraded under the condition of 60° C., indicating that high temperature has an effect on the stability of the free base.

TABLE 1

Results of stress testing on crystal form α

Stress testing on crystal form α Sample No: 1 (prepared in Example 1)

|  |  | Water (%) | Purity (%) | Maximum single impurity (%) | Total impurities (%) |
|---|---|---|---|---|---|
| Day 0 | 1 | 3.3 | 99.98 | 0.021 (RRT: 1.22) | 0.02 |
| Day 5 | 1-40° C. | 3.3 | 99.98 | 0.022 (RRT: 1.22) | 0.02 |
|  | 1-60° C. | 3.3 | 99.96 | 0.022 (RRT: 1.22) | 0.04 |
|  | 1-75% | 3.1 | 99.98 | 0.021 (RRT: 1.22) | 0.02 |
|  | 1-92.5% | 3.2 | 99.98 | 0.021 (RRT: 1.22) | 0.02 |
|  | 1-light irradiation | 3.1 | 99.93 | 0.051 (RRT: 0.93) | 0.07 |
| Day 10 | 1 | 3.2 | 99.98 | 0.022 (RRT: 1.22) | 0.02 |
|  | 1-40° C. | 3.3 | 99.98 | 0.022 (RRT: 1.22) | 0.02 |
|  | 1-60° C. | 3.3 | 99.96 | 0.020 (RRT: 1.22) | 0.04 |
|  | 1-75% | 3.1 | 99.98 | 0.022 (RRT: 1.22) | 0.02 |
|  | 1-92.5% | 3.2 | 99.98 | 0.022 (RRT: 1.22) | 0.02 |
|  | 1-light irradiation | 3.1 | 99.91 | 0.055 (RRT: 0.93) | 0.09 |

TABLE 2

Results of stress testing on crystal form β

Stress testing on crystal form β Sample No. 2 (prepared in Example 2)

|  |  | Water (%) | Purity (%) | Maximum single impurity (%) | Total impurities (%) |
|---|---|---|---|---|---|
| Day 0 | 2 | 4.4 | 99.97 | 0.017 (RRT: 1.22) | 0.03 |
| Day 5 | 2-40° C. | 4.4 | 99.97 | 0.020 (RRT: 1.22) | 0.03 |
|  | 2-60° C. | 4.3 | 99.83 | 0.151 (RRT: 0.93) | 0.17 |
|  | 2-75% | 4.4 | 99.97 | 0.019 (RRT: 1.22) | 0.03 |
|  | 2-92.5% | 4.5 | 99.97 | 0.018 (RRT: 1.22) | 0.03 |
|  | 2- light irradiation | 4.4 | 99.94 | 0.032 (RRT: 1.17) | 0.06 |
| Day 10 | 2 | 4.3 | 99.98 | 0.022 (RRT: 1.22) | 0.02 |
|  | 2-40° C. | 4.5 | 99.98 | 0.020 (RRT: 122) | 0.02 |
|  | 2-60° C. | 4.4 | 99.94 | 0.020 (RRT: 1.22) | 0.06 |
|  | 2-75% | 4.4 | 99.98 | 0.022 (RRT: 1.22) | 0.02 |
|  | 2-92.5% | 4.5 | 99.98 | 0.021 (RRT: 1.22) | 0.02 |
|  | 2- light irradiation | 4.5 | 99.80 | 0.177 (RRT: 0.93) | 0.20 |

TABLE 3

Results of stress testing on free base

| Sample | Study condition | Content (%) | Maximum single impurity (%) |
|---|---|---|---|
| Free base, Sample No. 3 (self-prepared) | Day 0 | 99.37 | 0.45 (RRT: 1.11) |
|  | 60° C., Day 5 | 96.77 | 2.14 (RRT: 0.44) |
|  | 40° C., Day 5 | 98.96 | 0.46 (RRT: 1.11) |
|  | 60° C., Day 10 | 95.15 | 2.88 (RRT: 0.43) |
|  | 40° C., Day 10 | 98.59 | 0.71 (RRT: 0.43) |

Preparation of free base: The free base was prepared using N-(3-chloro-4-fluorophenyl)-7-fluoro-6-nitro-4-quinazolin-amine as a starting material with reference to method of the patent publication WO2007085638.

Preparation of Solid Pharmaceutical Preparations

[Example 4] Preparation of Solid Pharmaceutical Preparations

Formulation 1:

| Ingredient | Amount |
| --- | --- |
| Crystal form α of Neptinib di-p-methylbenzenesulfonate 1.5 hydrate (Example 1) | 10 mg |
| Mannitol | 126 mg |
| Lactose | 50 mg |
| Crospovidone | 8 mg |
| Powder Silica gel | 2 mg |
| Glyceryl behenate | 4 mg |
| Total | 200 mg |

Method: The above ingredients were mixed and directly compressed in accordance with the conventional preparation methods.

Formulation 2:

| Ingredient | Amount |
| --- | --- |
| Crystal form α of Neptinib di-p-methylbenzenesulfonate 1.5 hydrate (Example 1) | 10 g |
| Mannitol | 80 g |
| Lactose | 74 g |
| Crospovidone | 20 g |
| Powder Silica gel | 6 g |
| Glyceryl behenate | 10 g |
| 3% HPMC | suitable amount |
| Total | 200 g |

Method: Crystal form α of Neptinib p-methylbenzenesulfonate 1.5 hydrate, mannitol, lactose, crospovidone were mixed well by equal quantity increment method, then added with the prepared HPMC solution to make soft material, granulated through a 20 mesh sieve, dried at 60° C. for 30 minutes, granulated with an 18 mesh sieve, added with powder silica gel and mixed well, and then packed into 2# capsules.

Formulation 3:

| Ingredient | Amount |
| --- | --- |
| Free base of Neptinib (self-prepared) | 10 mg |
| Mannitol | 126 mg |
| Lactose | 50 mg |
| Crospovidone | 8 mg |
| Powder Silica gel | 2 mg |
| Glyceryl behenate | 4 mg |
| Total | 200 mg |

Method: The above ingredients were mixed and directly compressed in accordance with the conventional preparation methods.

[Example 5] Control Stress Testing

Three batches of samples were prepared according to the process of Formulations 1~3 in Example 4. After the basic items were checked to be qualified, the samples were tested under the conditions of light irradiation, high temperature and high humidity to examine the appearance, content and dissolution of the samples. The results of stress testing showed that the samples are stable under the conditions of high temperature and light irradiation, and can be used as reference formulation and process. However, Formulation 3 is prone to absorb moisture under the conditions of 25° C., RH75% and 25° C., RH92.5%, and is easily degraded under the condition of light irradiation.

TABLE 4

| Tested item | Formulation 1 | Formulation 2 | Formulation 3 |
| --- | --- | --- | --- |
| Dissolution | good | good | poor |
| Compressibility | good | / | medium |
| Disintegration | good | medium | poor |

The purpose of developing the crystal form is mainly to solve the problem of dissolution and increase the dissolution rate. The dissolution test results according to the 2010 edition of the Pharmacopoeia showed that both Formulations 1 and 2 have a dissolution rate of more than 80% within 15 minutes, while Formulation 3 has a dissolution rate of less than 70% within 15 minutes. Based on the same excipients, each tested item of Formulation 1 is better than that of Formulation 3. The crystal form α and free base product have differences not only in melting point, solubility, crystal solubility, but also in stability, preparation dissolution, compressibility, disintegration, and so on. The latter has poor properties compared to the crystal form α of Neptinib di-p-methylbenzenesulfonate 1.5 hydrate of the invention.

While the description above refers to the preferred embodiments of the invention, various changes or modifications may be made by the persons skilled in the art without departing from the spirit of the invention, and should belong to the scope of the appended claims of the present invention.

What is claimed is:

1. A crystal form α of (E)-N-(4-((3-chloro-4-fluorophenyl)amino)-7-ethoxyquinazolin-6-yl)-4-(dimethylamino)but-2-enamide di-p-methylbenzenesulfonate represented by Formula (1), said crystal form α is (E)-N-(4-((3-chloro-4-fluorophenyl)amino)-7-ethoxyquinazolin-6-yl)-4-(dimethylamino)but-2-enamide di-p-methylbenzenesulfonate 1.5 hydrate, having an X-ray powder diffraction pattern with characteristic peaks at 2θ° of 5.0±0.2, 12.1±0.2, 14.5±0.2, 15.6±0.2, 17.6±0.2, 18.7±0.2, 20.1±0.2, 22.0±0.2, 25.4±0.2, 26.0±0.2 and 26.3±0.2, Formula (1)

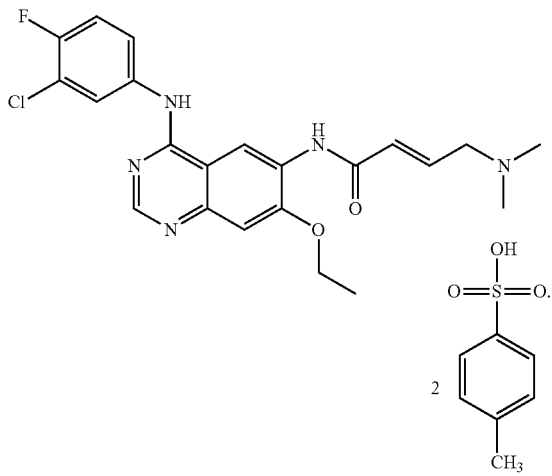

2. The crystal form α of (E)-N-(4-((3-chloro-4-fluorophenyl)amino)-7-ethoxyquinazolin-6-yl)-4-(dimethylamino)but-2-enamide di-p-methylbenzenesulfonate of claim 1, characterized in that, said 2θ° has an approximate relative intensity $I/I_0$ as the following value:

|  | 2θ° | $I/I_0$ |
|---|---|---|
| 1 | 5.0280 | 100% |
| 2 | 12.1417 | 13.90% |
| 3 | 14.5223 | 7.69% |
| 4 | 15.6252 | 8.19% |
| 5 | 17.6798 | 41.02% |
| 6 | 18.7496 | 25.08% |
| 7 | 20.1191 | 7.48% |
| 8 | 22.0733 | 8.89% |
| 9 | 25.4152 | 7.29% |
| 10 | 26.0953 | 7.39% |
| 11 | 26.3735 | 11.13% |

3. The crystal form α of (E)-N-(4-((3-chloro-4-fluorophenyl)amino)-7-ethoxyquinazolin-6-yl)-4-(dimethylamino)but-2-enamide di-p-methylbenzenesulfonate according to claim 1, characterized in that, said crystal form α has a maximum endothermic transition at about 133° C. in DSC scanning pattern.

4. The crystal form α of (E)-N-(4-((3-chloro-4-fluorophenyl)amino)-7-ethoxyquinazolin-6-yl)-4-(dimethylamino)but-2-enamide di-p-methylbenzenesulfonate according to claim 1, characterized in that, its thermogravimetric pattern shows a weight loss of 2.5% at 169° C.

5. The crystal form α of (E)-N-(4-((3-chloro-4-fluorophenyl)amino)-7-ethoxyquinazolin-6-yl)-4-(dimethylamino)but-2-enamide di-p-methylbenzenesulfonate according to claim 1, characterized in that, the infrared absorption spectrum using a potassium bromide disc comprises absorption peaks at about 3419, 3284, 3052, 2930, 2732, 2589, 1695, 1640, 1575, 1543, 1524, 1498, 1452, 1400, 1368, 1328, 1266, 1238, 1218, 1185, 1160, 1121, 1033, 1008, 814, 684, 568, 500 $cm^{-1}$.

6. A preparation method of the crystal form α of (E)-N-(4-((3-chloro-4-fluorophenyl) amino)-7-ethoxyquinazolin-6-yl)-4-(dimethylamino)but-2-enamide di-p-methylbenzenesulfonate of claim 1, comprising the steps of:
1) adding crude product of (E)-N-(4-((3-chloro-4-fluorophenyl)amino)-7-ethoxyquinazolin-6-yl)-4-(dimethylamino)but-2-enamide di-p-methylbenzenesulfonate into a mixed solvent of $C_1$-$C_4$ alkyl alcohol and water or into a mixed solvent of $C_3$-$C_4$ alkyl ketone and water, heating under reflux to achieve dissolution;
wherein the alkyl alcohol is selected from the group consisting of methanol, ethanol, propanol, isopropanol and butanol, and the volume ratio of alcohol to water is 11:1~20:1;
the alkyl ketone is selected from the group consisting of acetone, methyl ethyl ketone and butanone, and the volume ratio of ketone to water is 11:1~20:1; and
the weight volume ratio of the crude product to the solvent is 1 (g): 5~30 (ml), and the heating temperature is 50~80° C.; and
2) cooling the clear solution to precipitate, filtrating, collecting the precipitate, and drying the collected precipitate under reduced pressure to obtain the crystal form α;
wherein the precipitation is carried out for 2~8 hours, the precipitation temperature is 0~40° C., after the completion of precipitation and filtration, the drying temperature is 30~60° C.

7. The preparation method of claim 6, wherein in step (1), the alkyl alcohol is ethanol, the alkyl ketone is acetone, the weight volume ratio of the crude product to the solvent is 1:12 (g/ml), the mixed solvent of alcohol and water is heated to 70° C., the mixed solvent of ketone and water is heated to 60° C.;
in step (2), the precipitation is carried out for 4 hours, the precipitation temperature is 5~15° C., and the drying temperature is 45° C.

8. A pharmaceutical composition comprising the crystal form α of (E)-N-(4-((3-chloro-4-fluorophenyl)amino)-7-ethoxyquinazolin-6-yl)-4-(dimethylamino)but-2-enamide di-p-methylbenzenesulfonate of claim 1.

* * * * *